US006787363B2

(12) United States Patent
Cohen et al.

(10) Patent No.: US 6,787,363 B2
(45) Date of Patent: Sep. 7, 2004

(54) METHOD AND APPARATUS FOR HEMOSTASIS AND BLOOD MANAGEMENT

(75) Inventors: Eli Cohen, Skokie, IL (US); Irene A. Navickas, Northbrook, IL (US)

(73) Assignee: Haemoscope Corporation, Niles, IL (US)

( * ) Notice: Subject to any disclaimer, the term of this patent is extended or adjusted under 35 U.S.C. 154(b) by 0 days.

(21) Appl. No.: 10/261,331

(22) Filed: Oct. 1, 2002

(65) Prior Publication Data

US 2003/0069702 A1 Apr. 10, 2003

Related U.S. Application Data

(63) Continuation-in-part of application No. 09/974,044, filed on Oct. 10, 2001, which is a continuation-in-part of application No. 09/845,222, filed on Apr. 30, 2001, now Pat. No. 6,537,819, which is a continuation-in-part of application No. 09/591,371, filed on Jun. 9, 2000, now Pat. No. 6,613,573, which is a continuation of application No. 09/255,099, filed on Feb. 22, 1999, now Pat. No. 6,225,126.

(51) Int. Cl.[7] .............................................. G01N 33/86
(52) U.S. Cl. .......................... 436/69; 422/73; 73/64.41; 600/369; 705/2; 709/217
(58) Field of Search ...................... 436/63, 69; 435/13; 422/73; 73/64.41; 600/369; 705/2, 3; 700/266; 709/217

(56) References Cited

U.S. PATENT DOCUMENTS

| | | | | |
|---|---|---|---|---|
| 4,695,956 | A | * 9/1987 | LeVeen et al. ................. | 435/13 |
| 5,023,785 | A | 6/1991 | Adrion et al. | |
| 5,167,145 | A | * 12/1992 | Butler et al. ................. | 73/64.43 |
| 6,060,323 | A | * 5/2000 | Jina ............................ | 436/69 |
| 6,225,126 | B1 | * 5/2001 | Cohen et al. ................. | 436/69 |
| 6,537,819 | B2 | * 3/2003 | Cohen et al. ................. | 436/69 |
| 6,613,573 | B1 | * 9/2003 | Cohen ........................ | 436/69 |
| 2002/0178126 | A1 | * 11/2002 | Beck et al. ................... | 705/75 |
| 2002/0198740 | A1 | * 12/2002 | Roman et al. ................. | 705/3 |

OTHER PUBLICATIONS

Shore–Lesserson et al. Anesthesia and Analgesia (abstract), vol. 88 (2), Feb. 1999, p. 312.*
Frenette et al. Southern Medical Journal, vol. 91. No. 4, Apr. 1998, pp. 365–368.*
Nguyen et al. Arch. Pathol. Lab. Med., vol. 124, Apr. 2000, pp. 588–593.*
Joseph A. Caprini et al., *The Identification of Accelerated Coagulability*, Thrombosis Research, 1976, pp. 167–180, vol. 9, No. 2.
H. W. Grant et al., *Prediction of Neonatal Sepsis by Thromboelastography*, Pediatr. Surg. Int., 1997, pp. 289–292, vol. 12.
R. K. S. Whitta et al., *Thrombelastography Reveals Two Causes of Haemorrhage in HELLP Syndrome*, British Journal of Anaesthesia, 1995, pp. 464–468, vol. 74.
S. N. Mardel et al., *Reduced Quality of Clot Formation with Gelatin–based Plasma Substitutes*, British Journal of Anaesthesia, 1998, pp. 204–207, vol. 80.
Yoo Goo Kang, M.D., *Monitoring and Treatment of Coagulation*, pp. 151–173.
R. Rai et al., *Prepregnancy Thrombophilic Abnormalities are Associated with Subsequent Miscarriage*.

(List continued on next page.)

*Primary Examiner*—Maureen M. Wallenhorst
(74) *Attorney, Agent, or Firm*—Marshall, Gerstein & Borun LLP

(57) ABSTRACT

A procedure for hemostasis and blood management, particularly for cardiovascular procedures, provides: sampling instructions, i.e., when to draw blood samples and how to pre-treat the blood samples, a decision tree to assist the interpretation of hemostasis analysis results allowing for the identification of various coagulopathies, and treatment suggestions related to the hemostasis analysis results. The analysis, interpretation and identification may be conducted by a suitably programmed computer.

14 Claims, 5 Drawing Sheets

OTHER PUBLICATIONS

K. F. J. Ng et al., *In Vivo Effect of Haemodilution with Saline on Coagulation: A Randomized Controlled Trial*, British Journal of Anaesthesia, 2002, pp. 475–480, vol. 88, No. 4.

Christoph R. Kaufmann, M.D. et al., Usefulness *of Thrombelastography in Assessment of Trauma Patient Coagulation*, The Journal of Trauma: Injury, Infection, and Critical Care, 1997, pp. 716–722, vol. 42, No. 4.

D. Royston et al., *Reduced Haemostatic Factor Transfusion Using Heparinase–modified Thrombelastography During Cardiopulmonary Bypass*, British Journal of Anaesthesia, 2001, pp. 575–578, vol. 86, No. 4.

Paul D. Mongan, M.D. et al., *The Role of Desmopressin Acetate in Patients Undergoing Coronary Artery Bypass Surgery*, Anesthesiology, 1992, pp. 38–46, vol. 77.

J. A. Caprini et al., *Postoperative Hypercoagulability and Deep–vein Thrombosis After Laparoscopic Cholecystectomy*, Surgical Endoscopy, 1995, pp. 304–309, vol. 9.

Linda Shore–Lesserson, M.D. et al., *Thromboelastography–guided Transfusion Algorithm Reduces Transfusions in Complex Cardiac Surgery*, Anesth Analg. 1999, pp. 312–319, vol. 88.

Steve Von Kier et al., *Hemostatic Product Transfusions and Adverse Outcomes: Focus on Point–of–Care Testing to Reduce Transfusion Need*, Journal of Cardiothoracic and Vascular Anesthesia, 2000, pp. 15–21, vol. 14, No. 3, Suppl. 1.

S. V. Mallett et al., *Thrombelastography*, British Journal of Anaesthesia, 1992, pp. 307–313, vol. 69, No. 3.

Kenneth J. Tuman et al., *Effects of Progressive Blood Loss on Coagulation as Measured by Thrombelastography*, Anesth Analg, 1987, pp. 856–863, vol. 66.

Shiv K. Sharma et al., *Management of a Postpartum Coagulopathy Using Thrombelastography*, Journal of Clinical Anesthesia, 1997, pp. 243–247, vol. 9.

Yoogoo Kang, M.D. et al., *Epsilon–aminocaproic Acid for Treatment of Fibrinolysis During Liver Transplantation*, Anesthesiology, 1987, pp. 766–773, vol. 66, No. 6.

Yoogoo Kang et al., *Blood Coagulation During Liver, Kidney, Pancreas, and Lung Transplantation*, Perioperative Transfusion Medicine, 1998, pp. 471–492.

Shiv K. Sharma, M.D. et al., *Assessment of Changes in Coagulation in Parturients with Preeclampsia Using Thromboelastography*, Anesthesiology, 1999, pp. 385–390, vol. 90, No. 2.

S. Vig et al., *Thromboelastography: A Simple Screen for Hypercoagulable States, Hyperhomocysteinaemia and a Predictor of Failure Following Peripheral Arterial Intervention*, 1999.

Bruce D. Spiess, *Perioperative Coagulation Monitoring*, Perioperative Transfusion Medicine, 1998, pp. 239–257.

T. G. Ruttmann et al., *Haemodilution Induces a Hypercoagulable State*, British Journal of Anaesthesia, 1996, pp. 412–414, vol. 76.

K. F. G. Ng et al., *The Development of Hypercoagulability State, as Measured by Thrombelastography, Associated with Intraoperative Surgical Blood Loss*, Anaesthesia and Intensive Care, 1996, pp. 20–25, vol. 24, No. 1.

N. M. Gibbs et al., *Thrombelastographic Patterns Following Abdominal Aortic Surgery*, Anaesthesia and Intensive Care, 1994, pp. 534–538, vol. 22, No. 5.

Bruce D. Spiess et al., *Thromboelastography: A Coagulation–monitoring Technique Applied to Cardiopulmonary Bypass*, pp. 163–181.

Yoo Goo Kang, M.D. et al., *Intraoperative Changes in Blood Coagulation and Thrombelastographic Monitoring in Liver Transplantation*, Anesth Analg, 1985, pp. 888–896, vol. 64.

Brian P. Heather et al., *The Saline Dilution Test—A Preoperative Predictor of DVT*, Br. J. Surg., 1980, pp. 63–65, vol. 67.

Yoogoo Kang, M.D., *Thromboelastography in Liver Transplantation,*, Seminars in Thrombosis and Hemostasis, 1995, pp. 34–44, vol. 21, Suppl. 4.

* cited by examiner

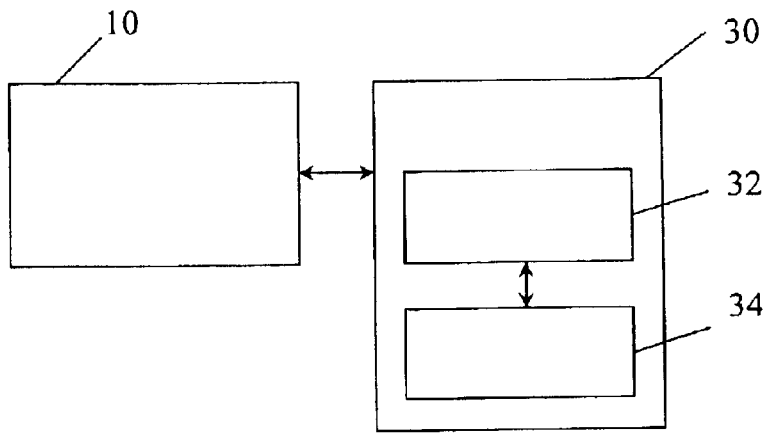

FIG. 4

| III. Treatment Guide | | |
|---|---|---|
| TEG® value | Hemostasis state | Common treatment |
| R between 11-14 min | ↓ clotting factors | x 2 FFP or 8 ml/kg[7,8,26] |
| R greater than 14 min | ↓↓ clotting factors | x 4 FFP or 16 ml/kg[1,5,26] |
| MA between 46 -54 mm | ↓ platelet function | .3μg/kg DDAVP[27,11] |
| MA between 41 -45 mm | ↓↓ platelet function | x5 platelet units[8,26] |
| MA at 40 mm or less | ↓↓↓ platelet function | x10 platelet units[5,26,8,1] |
| α less than 45° | ↓ fibrinogen level | 06 u/kg cryo[5] |
| LY30 at 7.5% or greater, C.I less than 1.0 | Primary fibrinolysis | antifibrinolytic of choice[5,1] |
| LY30 at 7.5% or greater, C.I greater than 3.0 | Secondary fibrinolysis | anticoagulant of choice[5,1,15] |
| LY30 less than 7.5%, C.I. greater than 3.0 | Prothrombotic state | anticoagulant of choice[11,15] |
| R less than 4 min or MA greater than 73 | Prothrombotic state | anticoagulant of choice[1,11,10,28] |

FIG. 7

| I. Sampling Protocol — All samples are Kaolin activated | | | If HIT, common treatment is with other thrombin-inhibitors such as Hirudin, Angiomax, etc., or a combination of platelet-inhibitor drugs with heparin. | |
|---|---|---|---|---|
| Sample # | When | Cup type | Measures | If TEG® testing shows: | Common Treatment |
| 1 & 2 | On induction | Split sample<br>• Heparinase bonded (blue) cup and pin<br>• *Plain* (clear) cup and pin<br>(If no heparin has been administered, place 5ul heparin [1,000USP/cc] in each cup to test for ATIII deficiency ) | Baseline hemostasis profile | Prothrombotic state AT III deficiency or others | • Treat with AT III or FFP<br>Antifibrinolytic drugs are contraindicated unless patient treated with Plavix, ReoPro, Aggrastat, or Integrilin, in which case Aprotinin is recommended |
| | | | | Evaluation for ATIII deficiency When heparin has been administered to either the patient or sample cup if Heparinase R and *Plain* R are the same, ATIII deficiency present | |
| 3 | At rewarming (approx 36°C) on CPB | Heparinase bonded (blue) cup and pin | Coagulopathy, if any, developed during bypass phase | Coagulopathy (see Decision Tree) | • Treat hyperfibrinolysis according to Treatment Guide below<br>Order blood product according to Treatment Guide below |
| 4 & 5 | 10 min post protamine | Split sample<br>• Heparinase bonded (blue) cup and pin<br>• *Plain* (clear) cup and pin | • Post-CPB hemostasis profile<br>• Heparin reversal | Heparinase R and *Plain* R are within normal limits, heparin is effectively reversed | None |
| | | | | Heparinase R normal, *Plain* R above normal limits, heparin is not completely reversed | Treat with Protamine |
| | | | | Coagulopathy (see Decision Tree) | See Treatment Guide below |
| 6 & 7 | Post op | Split sample<br>• Heparinase bonded (blue) cup and pin<br>• *Plain* (clear) cup and pin | Post-op hemostasis profile♦ (see Notes section below) | Normal | None |
| | | | | Coagulopathy / heparin rebound see Decision Tree / see above @ 4&5 | See Treatment Guide below |

FIG. 5

METHOD AND APPARATUS FOR HEMOSTASIS AND BLOOD MANAGEMENT

This patent is a continuation-in-part of U.S. patent application Ser. No. 09/845,222, filed Apr. 30, 2001, entitled "Method and Apparatus for Measuring Hemostasis," now U.S. Pat. No. 6,537,819 issued Mar. 25, 2003, which is a continuation of U.S. patent Application Ser. No. 09/255,099, filed Feb. 22, 1999, now U.S. Pat. No. 6,225,126 issued May 1, 2001, This application is also a continuation-in-pall of U.S. patent application Ser. No. 09/591,371, filed Jun. 9, 2000, entitled "Method and Apparatus for Monitoring Anti-Platelet Agents, " now U.S. Pat. No. 6,613,573 issued Sep. 2, 2003 and U.S. patent application Ser. No. 09/974,044, filed Oct. 10, 2001, entitled "Method and Apparatus for Diagnosing Hemostasis." The disclosures of all of the above-referenced U.S. patent and patent applications are hereby expressly incorporated herein by reference.

TECHNICAL FIELD

This patent relates generally to the field of hemostasis, and more particularly, this patent relates to a method and apparatus of hemostasis and blood product and pharmaceutical management.

BACKGROUND

Blood is the circulating tissue of an organism that carries oxygen and nutritive materials to the tissues and removes carbon dioxide and various metabolic products for excretion. Whole blood consists of pale yellow or gray yellow fluid, plasma, in which are suspended red blood cells, white blood cells, platelets, and hemostatic factors.

An accurate measurement of the ability of a patient's blood to coagulate and lyse in a timely and effective fashion is crucial to certain surgical and medical procedures. Accelerated (rapid) and accurate detection of abnormal coagulations is also of particular importance in respect of appropriate treatment to be given to patients suffering from clotting disorders and to whom it may be necessary to administer anticoagulants, antifibrinolytic agents, thrombolytic agents, anti-platelet agents, or blood components in a quantity which must clearly be determined after taking into account the abnormal components or "factors" of the patient's blood which may be contributing to the clotting disorder.

Hemostasis is a dynamic, extremely complex process involving many interacting factors, which include coagulation and fibrinolytic proteins, activators, inhibitors and cellular elements, such as platelet cytoskeleton, platelet cytoplasmic granules and platelet cell surfaces. As a result, during activation, no factor remains static or works in isolation. The end result of the coagulation process is a three-dimensional network of polymerized fibrin(ogen) fibers which together with platelet glycoprotein IIb/IIIa (GPIIb/IIIa) receptor bonding forms the final clot (FIG. 1). A unique property of this network structure is that it behaves as a rigid elastic solid, capable of resisting deforming shear stress of the circulating blood. The strength of the final clot to resist deforming shear stress is determined by the structure and density of the fibrin fiber network and by the forces exerted by the participating platelets.

Thus, the clot that develops and adheres to the damaged vascular system as a result of activated coagulation and resists the deforming shear stress of the circulating blood is, in essence a mechanical device, formed to provide a "temporary stopper," which resists the shear force of circulating blood during vascular recovery. The kinetics, strength, and stability of the clot, that is, its physical property to resist the deforming shear force of the circulating blood, determine its capacity to do the work of hemostasis, which is to stop hemorrhage without permitting inappropriate thrombosis. This is exactly what the Thrombelastograph® (TEG®) hemostasis analysis system, described below, is designed to do, which is to measure the time it takes for initial fibrin formation, the time it takes for the clot to reach its maximum strength, the actual maximum strength, and the clot's stability.

Blood hemostasis analyzer instruments have been known since Professor Helmut Hartert developed such a device in Germany in the 1940's. One type of blood hemostasis analyzer is described in commonly assigned U.S. Pat. Nos. 5,223,227 and 6,225,126, the disclosures of which are hereby expressly incorporated herein by reference. This instrument, the TEG® hemostasis analysis system, monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the kinetics, strength and stability of the clot provides information about the ability of the clot to perform "mechanical work," i.e., resisting the deforming shear stress of the circulating blood; in essence, the clot is the elementary machine of hemostasis, and the TEG® hemostasis analysis system measures the ability of the clot to perform mechanical work throughout its structural development. The TEG® hemostasis analysis system measures continuously all phases of patient hemostasis as a net product of whole blood components in a non-isolated, or static fashion from the time of test initiation until initial fibrin formation, through clot rate strengthening and ultimately clot strength through fibrin platelet bonding via platelet GPIIb/IIIa receptors and clot lysis.

While the ability to identify and measure all phases of patient hemostasis is now provided by, for example, the TEG® hemostasis analysis system, there is no comprehensive procedure for using this available data for the management of patient hemostasis and blood therapy. That is, there is no hemostasis analyzer guided procedure for the management of patient hemostasis and blood product or pharmaceutical therapy.

BRIEF DESCRIPTION OF THE DRAWINGS

FIG. 4 is a block diagram illustrating an apparatus for the management of patient hemostasis and blood product or pharmaceutical therapy.

FIG. 5 is a table illustrating the sampling procedure for a hemostasis analyzer guided procedure for the management of patient hemostasis and blood therapy.

FIG. 7 is a table illustrating a treatment guide providing guidance and treatment suggestions based on hemostasis analysis results.

DETAILED DESCRIPTION OF THE PREFERRED EMBODIMENTS

A procedure for hemostasis and blood management, particularly for cardiovascular procedures may include sampling instructions, i.e., when to draw blood samples and how to pre-treat the blood samples, a decision tree to assist the interpretation of hemostasis analysis results allowing for the identification of various coagulopathies, and treatment suggestions related to the hemostasis analysis results. While described herein particularly in connection with a cardiovascular application, the method and apparatus are generally applicable in any field using hemostasis analysis in the management of patient hemostasis and blood product usage.

Figure 1:
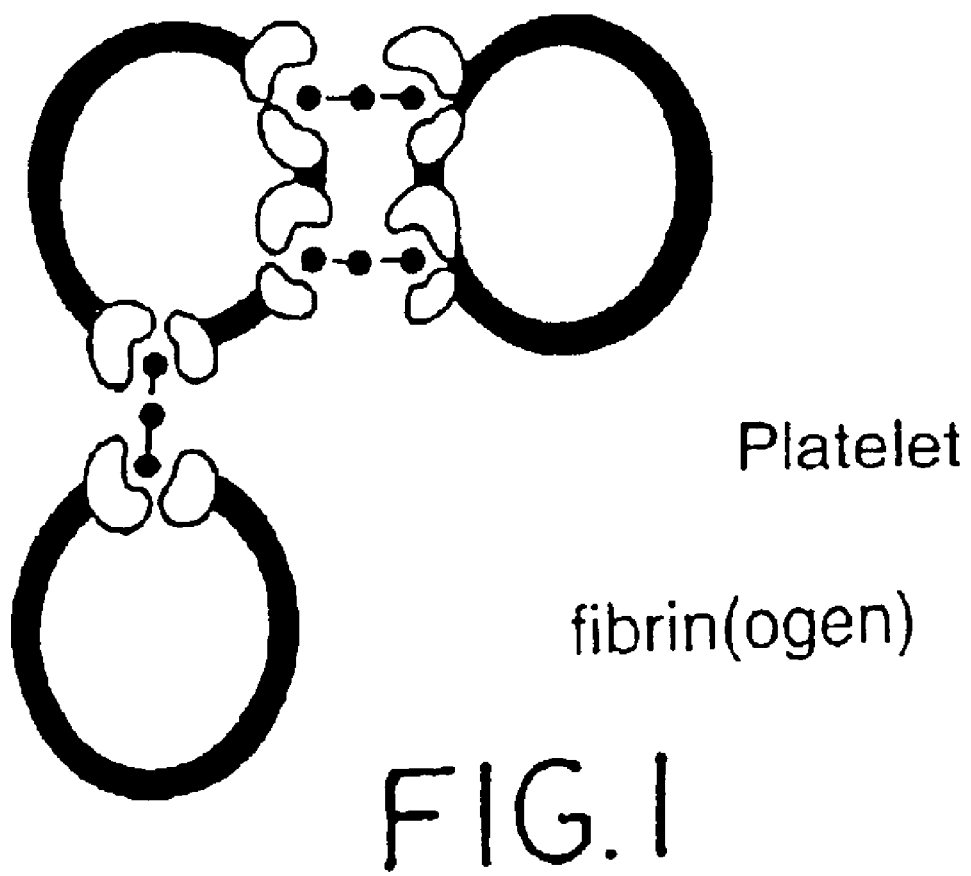
FIG. 1 is graphic illustration representing the mechanism of platelet aggregation.
Figure 2:
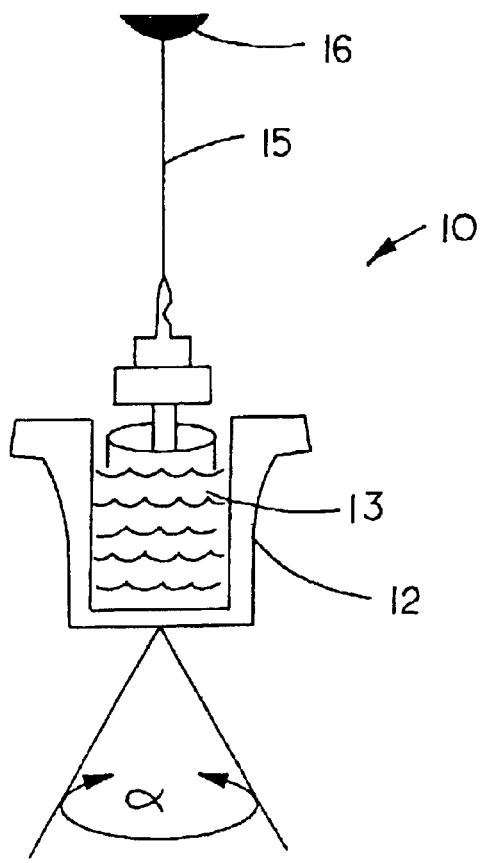
FIG. 2 is a schematic diagram of a blood coagulation analyzer in accordance with a preferred embodiment of the invention.

A procedure for management of hemostasis and blood product usage according to an embodiment of the invention, utilizes a blood hemostasis analyzer 10, such as the Thrombelastograph® (TEG®) hemostasis analysis system referenced above, to measure the clot's physical properties. An exemplary blood hemostasis analyzer 10 is described in detail in the aforementioned U.S. Pat. No. 6,225,126, and a complete discussion is not repeated here. With reference to FIG. 2, to assist in the understanding of the procedure, however, a brief description of the blood hemostasis analyzer 10 is provided. The blood hemostasis analyzer uses a special cylindrical cup 12 that holds a blood sample 13. The cup 12 is coupled to a drive mechanism that causes the cup to oscillate through an angle $\alpha$, preferably about 4°45'. Each rotation cycle lasts 10 seconds. A pin 14 is suspended in the blood sample 13 by a torsion wire 15, and the pin 14 is monitored for motion. The torque of the rotating cup 12 is transmitted to the immersed pin 14 only after fibrin-platelet bonding has linked the cup 12 and pin 14 together. The strength of these fibrin-platelet bonds affects the magnitude of the pin motion, such that strong clots move the pin 14 directly in phase with the cup motion. Thus, the magnitude of the output is directly related to the strength of the formed clot. As the clot retracts or lyses, these bonds are broken and the transfer of cup motion is diminished.

The rotation movement of the pin 14 is converted by a mechanical-electrical transducer 16 to an electrical signal, which can be monitored by a computer 30 (FIG. 4) including a processor 32 and a control program 34. The computer 30 is operable on the electrical signal to create a signature graph and a series of numeric parameters (collectively, hemostasis profile) corresponding to the measured clotting process. Additionally, the computer may include a visual display or be coupled to a printer to provide a visual representation of the hemostasis profile. Such a configuration of the computer is well within the skills of one having ordinary skill in the art, and while shown as a separate component may be integrated with the blood hemostasis analyzer.

Figure 3:
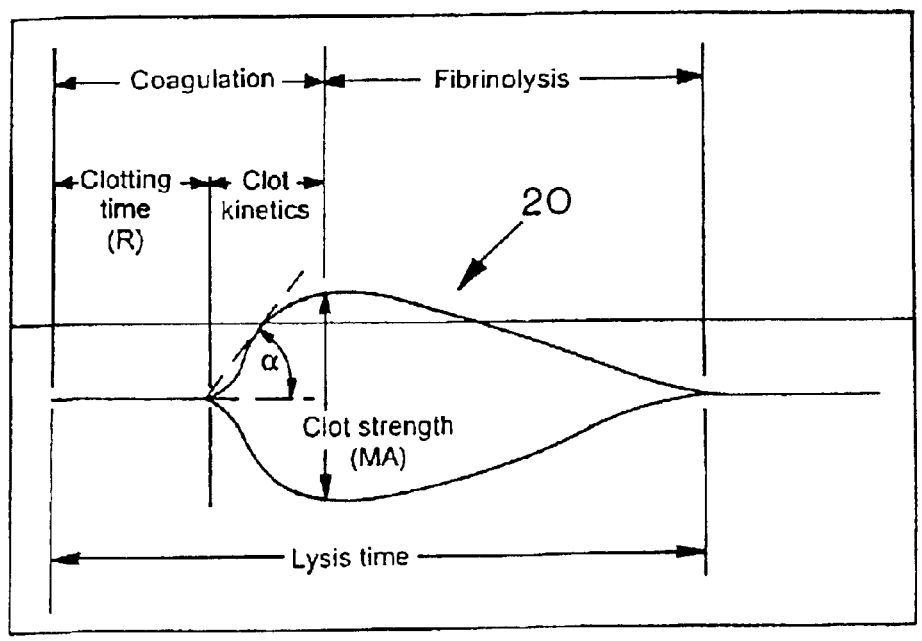
FIG. 3 is a plot illustrating a hemostasis profile generated by the blood coagulation analyzer shown in FIG. 2.

As shown in FIG. 3, the resulting hemostasis profile 20 is a measure of the time it takes for the first fibrin strand to be formed, the kinetics of clot formation, the strength of the clot and dissolution of the clot. Table I, below, provides definitions for several of these measured parameters.

TABLE I

| | |
|---|---|
| R | R time is the period of time of latency from the time that the blood was placed in the TEG ® hemostasis analyzer until the initial fibrin formation. |
| $\alpha$ | measures the rapidity of fibrin build-up and cross-linking (clot kinetics) |
| MA | MA, or Maximum Amplitude, is a direct function of the maximum dynamic properties of fibrin and platelet bonding via GPIIb/IIIa and represents the ultimate strength of the fibrin clot. |
| LY30 | LY30 measures the rate of amplitude reduction 30 minutes after MA and represents clot lysis. |

Of course, the procedure described herein may be adapted for use with hemostasis analysis machines that provide the above parameters, additional parameters or different parameters. Such machines are commercially available from various manufacturers.

Figure 6:
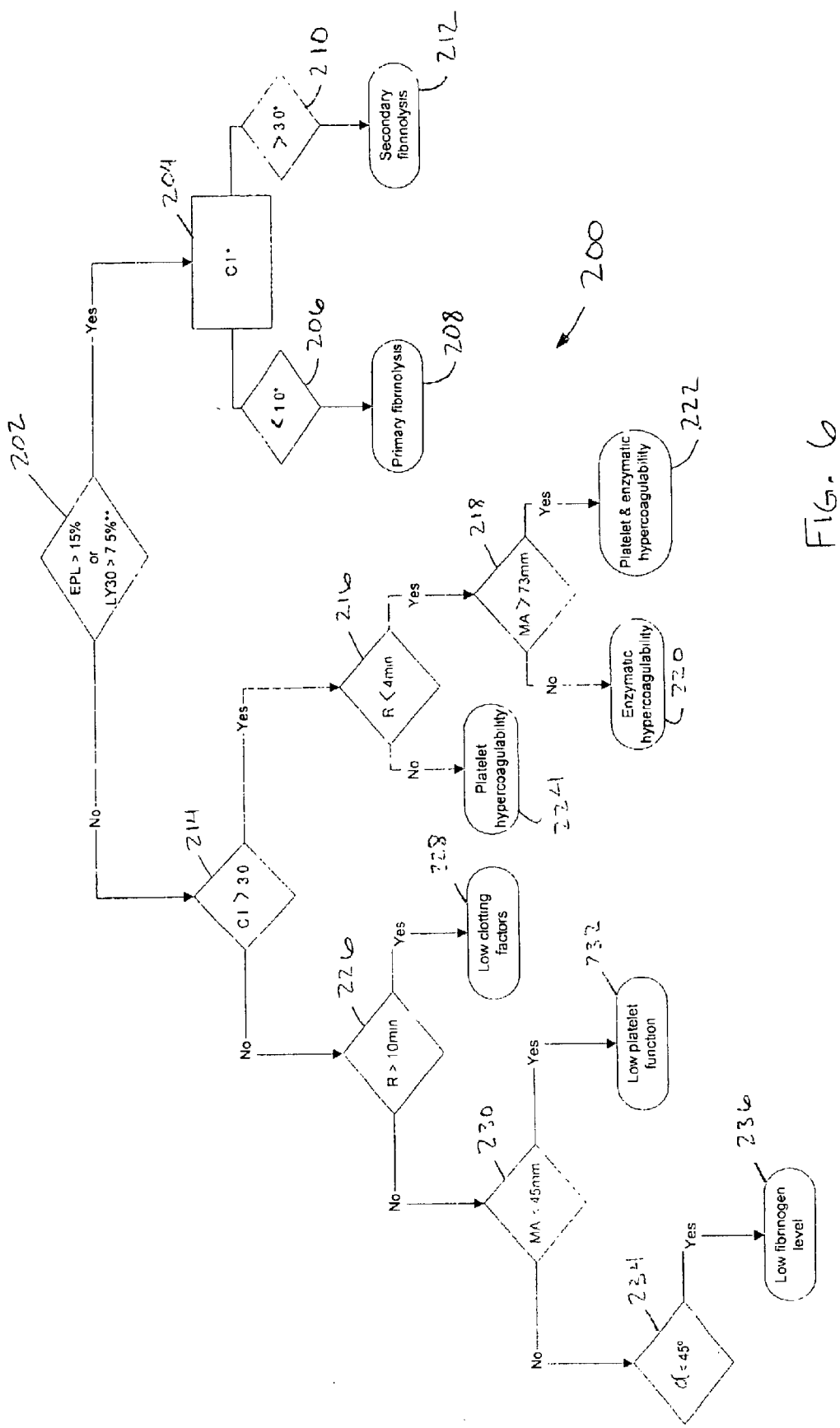
FIG. 6 is a flow chart illustrating a procedure for use with a hemostasis analyzer for guiding the management of patient hemostasis and blood therapy.

Referring to FIG. 5, a procedure 100 is outlined therein for hemostasis analyzer guided management of hemostasis and/or blood component usage, and to FIG. 6 wherein a decision tree 200 is defined to assist interpretation of the results provided by the hemostasis analyzer. The following description of a particular sampling protocol associated with a cardiovascular procedure provides an illustration example that may be used to develop additional sampling protocol for particular medical/surgical procedures. It will be appreciated that sampling protocols will necessarily be developed for each particular procedure, and that the described sampling protocol for a cardiovascular procedure may not be appropriate in connection with other procedures, such as for example, trauma treatment or organ transplantation.

The sampling instructions in the procedure indicate that all blood samples are to be treated with low concentrations of kaolin. Kaolin is a reagent that acts as a control surface that activates Factor XII and platelets of a blood sample, which provides faster results without losing the sensitivity of measuring all phases of patient hemostasis or detecting low concentrations of heparin.

Another issue in evaluating hemostasis and coagulopathy in connection with the herein described cardiovascular procedure is heparin effect. The sampling outlined in the procedure may call for use of heparinase—an enzyme that breaks down the heparin—so that patient hemostasis in the presence and absence of heparin can be measured. Some samples are split and analyzed with heparinase and some are analyzed without heparinase. Using this technique, it is possible to see if there is any heparin effect, residual heparin, or line contamination. If the results from both samples are similar, for example, both R values are within normal limits, then heparin has been effectively reversed. If, using the TEG hemostasis analyzer, R with heparinase is normal, but R without is elongated, then the heparin is not completely reversed.

Note that if the patient has not been treated with heparin as part of the cardiovascular procedure, coagulopathy should be evaluated based on the sample without heparinase. One of the advantages of TEG® hemostasis analysis is that samples can be run simulating in vivo conditions in the sample cup—and should. So, in the case where the patient is not on heparin, hemostasis assessment should be based on the sample without heparinase.

According to the exemplary cardiovascular sampling protocol 100 outlined in FIG. 4, samples are drawn at four time points:

Baseline on induction

At rewarming (about 36°)

Ten minutes post protamine

Post surgery.

Baseline Sample

When the patient comes into the operating room a baseline sample is run as a starting point of the measuring stick for patient hemostasis and to establish whether the patient is hypercoagulable or has a tendency to bleed. This specimen is split into two aliquots, sample 1 and sample 2. One of the samples is analyzed using heparinase and one is analyzed without heparinase to check for heparin effect as well as for antithrombin III (ATIII) deficiency. Conveniently, the TEG® hemostasis analysis system allows for the use of plain sample cups and pins (clear cups) and sample cups and pins treated with heparinase (blue cups).

ATIII deficiency is easily shown if the heparinase R and non-heparinase R are the same when heparin has been administered either to the patient or to the sample in the cup.

ATIII deficiency is typically treated with ATIII or fresh frozen plasma (FFP). If the patient is hypercoagulable, antifibrinolytic drugs are contraindicated unless the patient has been treated with platelet inhibitors or has the tendency to bleed, in which case Aprotinin (Trasylol) is suggested.

At Rewarming

A sample, sample 3, is drawn at rewarming of the patient—approximately 36°—and shows the maximum expression of any coagulopathy that has developed during the procedure. Sample 3 is another notch on the hemostasis measuring stick for two effects:

the effect of the trauma of surgery on the patient the net effect of extracorporeal surfaces on hemostasis at a time when the blood has been on the pump for the longest time.

Extra-corporeal devices, in general, reduce hypercoagulability, but in the case of off pump coronary artery bypass (OPCAB) the patient becomes more hypercoagulable. The results from sample 3 are typically used to determine which drug products are required (and are usually administered at this time), and which blood products should be ordered for administration later.

The MA value of sample 3 is typically 5 to 7 mm lower at this point than the post protamine sample, described below, and this should be taken into consideration when evaluating the results. This is particularly true if the value is borderline low and platelets, which may not be needed, are being considered.

Usually, if rewarming values are normal, patient hemostasis will continue to be normal post surgery. However, the patient should still be monitored for residual heparin effect (post protamine), surgical bleeding, or at a later time for hypercoagulability.

10 Minutes Post Protamine

At this point, the patient has been treated with protamine to neutralize the heparin. This is a split sample, samples 4 and 5, used to compare the R with and without heparinase as a check for residual heparin. If the R's are equal for both sample 4 and sample 5, the heparin has been effectively neutralized. If the R without heparinase is longer than with, there is residual heparin.

Samples 4 and 5 also show the importance of the baseline sample, since the degree of change from baseline is significant. Where the change between the baseline MA and the post protamine MA is great, that is, a baseline MA that is high and falls to the borderline transfusion trigger value, is a predictor of greater oozing or bleeding than where the difference is smaller, and should be considered for treatment accordingly.

If the sample post protamine shows coagulopathy, most likely it is consistent with what was already observed while the patient was on the bypass pump.

Post Surgery

After surgery—one hour in the intensive care unit (ICU)—the sample provides a wealth of information. Perhaps the most important is that it is a check if treatment so far was effective. It is also the point at which to evaluate the amount of chest tube drainage and heparin rebound. If there has been an increase in the hypercoagulability, consideration should be given to whether to anticoagulate or to order more testing, such as at 2 hour intervals.

If the hemostasis analysis results look normal, i.e., they do not indicate any coagulopathy, but the patient is bleeding, then there is likely no coagulopathy. It's most likely surgical bleeding. However, consideration should be given to von Willebrand's disease or acquired von Willebrand's factor (VWF) deficiency. In this case, the clot is fully functional, but it cannot adhere to the damaged vascular site, due to poor platelet-to-sub endothelial collagen bonding. Surgical bleeding can typically be differentiated from VWF deficiency by the greater rate of bleeding associated with surgical bleeding. However, because of the increased risk to the patient in misdiagnosing VWF deficiency as surgical bleeding, consider treating the patient with FFP or cryoprecipitate (cryo) (which carries VWF as part of Factor VIII) to confirm, or with desmopressin acetate (DDAVP) to stimulate the release of VWF by the endothelium. If the bleeding is diminished by treatment, VWF deficiency is indicated. If bleeding continues despite treatment, surgical bleeding is indicated, and the FFP or cryo is needed in any case for volume replacement.

When the surgical site is small, surgical bleeding may be remedied clinically with continuous product transfusion, and this remedy should be considered before reexploration. If the site is large, reexploration may be required to remedy the problem.

Thus, according to one procedure in accordance with the invention, samples are drawn at multiple time points, and these samples may be treated with kaolin to achieve faster analysis results. Comparison of heparinase treated samples to non-treated samples evaluates degree of heparin effect, residual heparin effect, heparin rebound, and patient hemostasis in the presence of heparin. Following this sampling protocol gives a complete picture ofthe patient's hemostasis as it shifts from baseline through surgery and into the ICU. These samples, when evaluated against the decision tree 200 (FIG. 6), provide additional answers regarding treatment of developing coagulopathies or surgical bleeding. While the above-described sampling protocol is primarily adapted for use in connection with a cardiovascular procedure, the decision tree 200 has general applicability to the diagnosis and treatment of coagulopathies. The decision tree 200 may be implemented as a guide associated with the blood hemostasis analyzer. Conveniently, the decision tree 200 may be implemented as part of the control program 34 used by the computer 30 to control operation of the blood hemostasis analyzer. Alternatively, the blood hemostasis analyzer may include communication capability and may communicate with a remote computing device, such as a remotely located computer, a handheld computer and the like, via the Internet or other communication network using wired and/or wireless connections. An arrangement of a blood hemostasis analyzer to communicate with a remote computer that may be used is described in the aforementioned U.S. patent application Ser. No. 09/974,044 the disclosure of which is incorporated herein.

The decision tree 200 helps identify the coagulopathy and in the case of hyperfibrinolysis, can distinguish between primary and secondary fibrinolysis. In the case of hypercoagulability, it may be necessary to use a hemostasis analysis technique that can distinguish between platelet-induced vs. enzymatic hypercoagulability. The TEG hemostasis analysis system allows for making this distinction.

In applying hemostasis analysis results to the decision tree 200, the first evaluation is for hyperfibrinolysis. Using TEG hemostasis analysis, there is an indication of hyperfibrinolysis where LY30>7.5%. If LY30 isn't yet available, EPL—an estimate of lysis—may be used instead, with a value of >15% indicating fibrinolysis (202).

If the sample shows fibrinolysis next the coagulation index (CI) is evaluated (204). If the coagulation index is less than one, CI<1 (206), the patient is not hypercoagulable, and this is primary fibrinolysis (208). If the sample shows fibrinolysis and the coagulation index is greater than 3, CI>3 (210), indicating hypercoagulability, then it is secondary fibrinolysis (212)—it is secondary to the hypercoagulability. Making the determination of primary fibrinolysis then becomes easy—if it is not secondary primary fibrinolysis (212), it is primary (210).

The D-dimer test is frequently used to diagnose fibrinolysis, but it gives an elevated result for both types of fibrinolysis, and this is extremely risky. It leads to a misdiagnosis, and the penalty to the patient of misdiagnosing secondary fibrinolysis as primary can be fatal. For example, suppose a mistaken diagnosis of secondary fibrinolysis is treated with antifibrinolytics such as Amicar. This treatment in effect blocks the pathway to break down the clot and therefore increases the probability of a repeat ischemic event.

On the other hand, if a mistaken diagnosis of secondary fibrinolysis is treated with anticoagulants—making the patient bleed more—the penalty is not as great. Continued or increased bleeding can be neutralized with drugs, as in neutralizing heparin with protamine. Antifibrinolytic drugs such as Amicar may then be given to treat the primary fibrinolysis.

On the other branch of the decision tree 200, when LY30<7.5 (202) (no hyperfibrinolysis), evaluation is made first for hypercoagulability. A coagulation index greater than 3, CI>3 (214) indicates hypercoagulability. The next step is to decide between enzymatic and platelet hypercoagulability. If using the TEG® hemostasis analysis system a check of R is made. If R is short, for example less than 4 minutes (216), it's enzymatic (220). In addition, if R is short (216) and platelet function is high, MA is high, greater than 73 mm (218), it is due to high enzymatic reaction and high platelet activation (222). On the other hand, if R is normal and MA is high, hypercoagulability is due to high platelet function (224). Treatment with platelet inhibitors such as aspirin, ADP inhibitors such as Plavix, or GPIIb/IIIa inhibitors such as ReoPro, Integrilin, and Aggrastat is indicated.

When CI<3 (214)—not hypercoagulable—and R is elongated, greater than 10 minutes (226) the first priority is to normalize the R. This long R is due to low clotting factors (228) from coagulopathy or hemodilution resulting in a low rate of thrombin formation, which activates the platelets and cleaves the soluble fibrinogen into fibrin. The best treatment is FFP for clotting factors. If R is normal—no hypercoagulability—and MA is <45 mm (230) indicating low platelet function (232), typical treatment is with DDAVP or one unit of platelets. If MA<48 mm, platelets should be administered appropriately as described below. If R and MA appear normal, but alpha is low (a<45°, 234), you can correct for low fibrinogen level (236) by treating with cryo, which not only contains high concentrations of fibrinogen, but also has high concentrations of factor VIII and factor XIII.

In some situations, R may be slightly elongated post protamine due to hemodilution. In such cases, the patient is usually not bleeding and no treatment is needed. If the hemostasis analysis results are normal but the patient is still oozing, that should gradually diminish.

The decision tree 200 arranges the evaluation criteria in a logical manner and is used to arrive, in a systematic way, at a coagulopathy diagnosis. All the hemostasis parameters are interdependent, and it is necessary to evaluate the parameters relative to each other, in addition to the patient's clinical status and bleeding state, to determine if a coagulopathy is present, which coagulopathy it is, and how to treat it. FIG. 7 illustrates a treatment guide 300 that maybe part of the protocol to assist in this last step.

Referring to FIG. 7, the treatment guide 300 provides guidance and a treatment suggestion based on hemostasis analysis results. Knowing the part of the hemostasis process that is represented by each of the parameters leads to the hemostasis state of the sample, and, thus, knowing the magnitude of a parameter indicates the level of coagulopathy. Having identified this, then appropriate treatment in the right dosage becomes easier to determine.

As an illustration, using the decision tree, an R value over 10 mm indicates low clotting factors. The treatment guide 300 expands on that and indicates that R between 11 and 14 shows slightly low clotting factors and should be treated with 2 units of FFP, while R>14 indicates more severe shortage of clotting factors and should be treated with twice that—4 units of FFP.

Similarly, MA values less than 55 mm indicate low platelet function and three categories of MA are shown for increasing levels of platelet dysfunction, with corresponding increasing therapy. Slightly low levels can be treated with DDAVP, one unit of platelets, or nothing at all as it may be possible to simply wait for the patient's own platelets to recover.

The treatment guide 300 gives specific guidance in how to treat the coagulopathies that are already present or develop during and after surgery. The degree of coagulopathy can be evaluated by the magnitude of the hemostasis analysis values reported, and treatment determined and adjusted based on those values.

The decision tree 200 and treatment guide 300 may be further used to test potential treatment protocols prior to administering the treatment to a subject. The efficacy of a proposed treatment can be tested by adding the pharmaceutical or blood product to a blood sample in vitro. Prior in vitro evaluation of the treatment protocol can provide an indication of the efficacy on patient hemostasis in vivo. In this manner, hemostasis and blood product usage is managed by first testing according to a sampling protocol, determining a coagulopathy based upon a decision tree and identifying a treatment in view of a treatment guide. The propose treatment may then by tested in vitro to confirm efficacy. It will be appreciated that a post treatment sampling and testing protocol The invention has been described in terms of several preferred embodiments. One of skill in the art will appreciate that the invention may be otherwise embodied without departing from its fair scope, which is set forth in the subjoined claims.

We claim:

1. A method for hemostasis and blood product management during the course of a medical procedure, the method comprising the steps of:

obtaining a plurality of blood samples from a subject of the medical procedure, of the plurality of blood samples being drawn at pre-procedural, intra-procedural and post-procedural time periods;

subjecting each of the plurality of blood samples to a hemostasis analysis to provide a hemostasis parameter associated with the each respective blood sample providing logically organized results analysis criteria in the form of a decision tree;

evaluating the at least one hemostasis parameter in accordance with the logically organized results analysis criteria to provide at least one evaluation result; and selecting a hemostasis and blood management protocol based upon the at least one evaluation result.

2. The method of claim 1, further comprising the step of providing a computer controlled hemostasis analysis device, the hemostasis analysis device including a memory and a processor capable of data analysis, and wherein the memory includes the results analysis criteria and the step of evaluating the hemostasis parameter is performed by the processor.

3. The method of claim 2, wherein the step of subjecting the plurality of blood samples to a hemostasis analysis is performed by the hemostasis analysis device.

4. The method of claim 1, wherein a hemostasis analysis device provides the hemostasis parameter, and wherein the results analysis criteria is at a location remote from the hemostasis analysis device, the method further comprising communicating the at least one hemostasis parameter to the location.

5. The method of claim 4, wherein the step of communicating the at least one hemostasis parameter comprises communication the at least one hemostasis parameter via the Internet.

6. The method of claim 4, wherein the step of communicating the at least one hemostasis parameter comprises communicating the at least one hemostasis parameter via one of a wired and a wireless communication link.

7. The method of claim 1, wherein the medical procedure comprises a cardiovascular medical procedure.

8. The method of claim 1, wherein the results analysis criteria comprises a decision tree for guiding hemostasis management.

9. The method of claim 8, wherein the decision tree is implemented within a controller of a blood hemostasis analyzer used to provide the at least one hemostasis parameter.

10. An apparatus for hemostasis and blood management comprising:

a blood hemostasis analyzer for providing a hemostasis parameter a computer comprising a controller, control program and a memory, wherein saidcomputer is coupled to the hemostasis analyzer through a communication link; and a decision tree associated with the blood hemostasis analyzer, the decision tree including analysis criteria relating a coagulopathy with the hemostasis parameter the decision tree being embodied within the control program of the computer and the controller being operable in response to the control program to relate the coagulopathy to the hemostasis parameter.

11. The apparatus of claim 10, wherein the communication link comprises one of a wired and a wireless communication link.

12. The apparatus of claim 10, wherein the communication link comprises a communication network.

13. An apparatus for hemostasis and blood management comprising:

means for determining a hemostasis parameter from a blood sample;

means for analyzing the hemostasis parameter relative to logically organized analysis criteria analysis criteria for providing and analysis result that related the hemostasis parameter to a coagulopathy; and means for identifying a hemostasis and blood management protocol based upon the analysis result, wherein a communication link serves to couple the means for determining, the means for analyzing and the means for identifying.

14. The apparatus of claim 13, wherein the means for analyzing and the means for identifying comprise a computer including a control program, the control program including an algorithm implementing the decision tree.

* * * * *

UNITED STATES PATENT AND TRADEMARK OFFICE
CERTIFICATE OF CORRECTION

PATENT NO. : 6,787,363 B2
DATED : September 7, 2004
INVENTOR(S) : Eli Cohen et al.

It is certified that error appears in the above-identified patent and that said Letters Patent is hereby corrected as shown below:

Title page,
Item [*] Notice, please insert -- This patent is subject to a terminal disclaimer. --

Column 8,
Line 67, please delete "of the plurality" and insert -- the plurality --

Column 9,
Lines 3-5, please "subjecting each of the plurality of blood samples to a hemostatsis analysis to provide a hemostasis parameter associated with the each respective blood sample" and insert -- subjecting each of the plurality of blood samples to a hemostasis analysis to provide at least one hemostasis parameter associated with each respective blood sample; --
Line 25, please delete "the hemostasis parameter" and insert -- the at least one hemostasis parameter --
Line 32, please delete "communication" and insert -- communicating --

Column 10,
Lines 7-9, please delete "hemostasis parameter a computer comprising a controller, control program and a memory, wherein saidcomputer" and insert -- hemostasis parameter, a computer comprising a controller, control program and a memory; wherein said computer --
Lines 29-30, please delete "analysis criteria analysis criteria for providing and analyis result that related the hemostasis parameter" and insert -- analysis criteria in a decision tree for providing an analysis result that relates the hemostasis parameter --

Signed and Sealed this

Fifteenth Day of March, 2005

JON W. DUDAS
*Director of the United States Patent and Trademark Office*